(12) United States Patent
Karri et al.

(10) Patent No.: US 11,568,983 B2
(45) Date of Patent: Jan. 31, 2023

(54) TRIAGE VIA MACHINE LEARNING OF INDIVIDUALS ASSOCIATED WITH AN EVENT

(71) Applicant: International Business Machines Corporation, Armonk, NY (US)

(72) Inventors: Venkata Vara Prasad Karri, Visakhapatnam (IN); Girish Padmanabhan, Pune (IN); Rajesh Patil, Westborough, MA (US); Sampath Kumar Pulupula Venkata, Visakhapatnam (IN)

(73) Assignee: International Business Machines Corporation, Armonk, NY (US)

( * ) Notice: Subject to any disclaimer, the term of this patent is extended or adjusted under 35 U.S.C. 154(b) by 672 days.

(21) Appl. No.: 16/575,830

(22) Filed: Sep. 19, 2019

(65) Prior Publication Data

US 2021/0090720 A1 Mar. 25, 2021

(51) Int. Cl.
*G16H 40/20* (2018.01)
*H04W 76/50* (2018.01)
(Continued)

(52) U.S. Cl.
CPC .............. *G16H 40/20* (2018.01); *G06N 20/00* (2019.01); *H04L 63/302* (2013.01);
(Continued)

(58) Field of Classification Search
CPC ...... G06N 20/00; G16H 40/20; H04L 63/302; H04M 2242/04; H04M 3/5116;
(Continued)

(56) References Cited

U.S. PATENT DOCUMENTS

| 8,024,330 B1 | 9/2011 | Franco |
| 8,881,990 B2 | 11/2014 | Hunt |

(Continued)

FOREIGN PATENT DOCUMENTS

| CN | 105701359 A | * | 6/2016 |
| CN | 106506441 A | * | 3/2017 |

(Continued)

OTHER PUBLICATIONS

Meiz, Rachel, "Communication App Works Without a Cellular Network", MIT Technology Review, Dec. 10, 2014, 9 pages, <https://www.technologyreview.com/s/533081/communication-app-works-without-a-cellular-network/[May 13, 2019, 2:49:37 PM]>.

*Primary Examiner* — Matthew C Sams
(74) *Attorney, Agent, or Firm* — Monchai Chuaychoo (57) ABSTRACT

An approach for triaging injured individuals. The system receives data from one or more mobile computing devices, wherein data comprises a first location associated with an event, video data and audio data and the system analyze the received data. And the system matches one or more medical personnel with one or more injured individual of the event and generates an output list, wherein the output list comprises a second location to transport the injured individual. Furthermore, the system notifies one or more transportation personnel of the second location for transport and notifies one or more personnel at the second location of the arrival of the injured individual.

20 Claims, 4 Drawing Sheets

(51) Int. Cl.
*H04W 4/44* (2018.01)
*H04W 4/90* (2018.01)
*H04L 9/40* (2022.01)
*H04M 3/51* (2006.01)
*G06N 20/00* (2019.01)
*H04W 4/029* (2018.01)

(52) U.S. Cl.
CPC ......... *H04M 3/5116* (2013.01); *H04W 4/029* (2018.02); *H04W 4/44* (2018.02); *H04W 4/90* (2018.02); *H04W 76/50* (2018.02); *H04M 2242/04* (2013.01)

(58) Field of Classification Search
CPC ......... H04W 4/029; H04W 4/44; H04W 4/90; H04W 76/50
See application file for complete search history.

(56) References Cited

U.S. PATENT DOCUMENTS

| | | | | |
|---|---|---|---|---|
| 8,968,197 | B2 * | 3/2015 | Friedlander | A61B 5/0022 |
| | | | | 701/515 |
| 10,368,806 | B2 * | 8/2019 | Kim | B60Q 1/50 |
| 2007/0102527 | A1 * | 5/2007 | Eubank | H04M 1/72418 |
| | | | | 340/539.18 |
| 2009/0198733 | A1 * | 8/2009 | Gounares | G16Z 99/00 |
| 2011/0071880 | A1 | 3/2011 | Spector | |
| 2013/0005294 | A1 * | 1/2013 | Levinson | G08B 25/005 |
| | | | | 455/404.1 |
| 2013/0052983 | A1 * | 2/2013 | Fletcher | H04L 67/303 |
| | | | | 455/404.2 |
| 2014/0368601 | A1 * | 12/2014 | deCharms | H04L 67/26 |
| | | | | 348/14.02 |
| 2016/0140299 | A1 * | 5/2016 | Al Harbi | G16Z 99/00 |
| | | | | 705/2 |
| 2018/0144639 | A1 * | 5/2018 | Kumar | G08G 1/205 |
| 2018/0197352 | A1 * | 7/2018 | Ganesh | G06V 20/584 |
| 2018/0288224 | A1 * | 10/2018 | Dizengof | H04W 4/90 |
| 2019/0007819 | A1 | 1/2019 | Marchiol | |
| 2019/0047578 | A1 * | 2/2019 | Swan | G06V 20/597 |
| 2019/0174289 | A1 * | 6/2019 | Martin | H04W 4/21 |
| 2020/0074222 | A1 * | 3/2020 | Guo | G06N 3/08 |

FOREIGN PATENT DOCUMENTS

| | | | |
|---|---|---|---|
| CN | 106600994 A | * | 4/2017 |
| CN | 106778038 A | | 5/2017 |
| CN | 206422859 U | * | 8/2017 |
| CN | 107451723 A | * | 12/2017 |
| CN | 107480851 A | * | 12/2017 |
| WO | WO-2017044972 A1 | * | 3/2017 |

* cited by examiner

TRIAGE VIA MACHINE LEARNING OF INDIVIDUALS ASSOCIATED WITH AN EVENT

BACKGROUND

The present invention relates generally to the field of emergency response systems and methods, and more particularly to leveraging AI (Artificial Intelligence) to triage patients based on one or more responder profiles and other factors.

Emergency medical services (EMS) are emergency services which treat illnesses and injuries that require an urgent medical response, providing out-of-hospital treatment and transport to definitive care. For example, EMS could be called to an automobile accident site.

Initially, EMS provides treatment on the scene (e.g., auto accident, etc.) to those in need of urgent medical care. If necessary, they are tasked with transferring the patient/victim to the next point of care. The next point of care could be an emergency department of a hospital. Members of an EMS service are trained in various capacities such as basic first aid and basic life support. Some members are trained with advance life support skills

SUMMARY

Embodiments of the present invention disclose a computer-implemented method, computer program product and a computer system for triaging injured individuals comprising: receiving, by one or more computer processors, data from one or more mobile computing devices associated with one or more injured individuals at an event, wherein data comprises a first location, video data and audio data; analyzing, by the one or more computer processors, the received data; matching, by the one or more computer processors, one or more medical personnel with the one or more injured individuals of the event; generating, by the one or more computer processors, an output list, wherein the output list comprises a second location to transport at least one of the one or more injured individuals; notifying, by the one or more computer processors, one or more transportation personnel of the second location for transporting the at least one of the one or more injured individuals; and notifying, by the one or more computer processors, one or more healthcare facility personnel at the second location of the arrival of the at least one of the one or more injured individuals.

The computer program product may include one or more computer readable storage media and program instructions stored on the one or more computer readable storage media, the program instructions comprising: program instructions to receive data from one or more mobile computing devices associated with one or more injured individuals at an event, wherein data comprises a first location, video data and audio data; program instructions to analyze the received data; program instructions to match one or more medical personnel with the one or more injured individuals of the event; program instructions to generate an output list, wherein the output list comprises a second location to transport at least one of the one or more injured individuals; program instructions to notify one or more transportation personnel of the second location for transporting the at least one of the one or more injured individuals; and program instructions to notify one or more healthcare facility personnel at the second location of the arrival of the at least one of the one or more injured individuals.

The computer system may include one or more computer processors; one or more computer readable storage media; program instructions stored on the one or more computer readable storage media for execution by at least one of the one or more computer processors, the program instructions comprising: program instructions to receive data from one or more mobile computing devices associated with one or more injured individuals at an event, wherein data comprises a first location, video data and audio data; program instructions to analyze the received data; program instructions to match one or more medical personnel with the one or more injured individuals of the event; program instructions to generate an output list, wherein the output list comprises a second location to transport at least one of the one or more injured individuals; program instructions to notify one or more transportation personnel of the second location for transporting the at least one of the one or more injured individuals; and program instructions to notify one or more healthcare facility personnel at the second location of the arrival of the at least one of the one or more injured individuals.

DETAILED DESCRIPTION

Embodiments of the present invention can provide an efficient and intelligent approach of triaging injured individuals due to unfortunate events (e.g., automobile accidents, train derailment, airplane crash, boat collision/accidents, etc.) and coordinating an appropriate emergency responder to render aid based on the medical condition of those injured individuals. For example, a multi-car accident occurred where there is one injured individual in need of medical assistance. The system, through AI (Artificial Intelligence), specifically via deep learning, can ascertain the state of an injured individual using images (retrieved from mobile devices) of the accident location and audio clues (retrieved from mobile devices) from the injured individual and other people at the accident location. Furthermore, the system can identify the appropriate doctor, clinics or certified emergency responders nearest to the accident site or location of the injured individual. For example, an injured individual has chest/heart trauma. The system can find a doctor nearby that specializes in treating cardiac/thoracic trauma and routes the emergency vehicle (i.e., ambulance) to the location of that particular doctor.

In some embodiments, the system can notify the appropriate relatives of the injured individuals. The system can leverage social media and/or mobile media contacts, with user permission, based on the situation. For example, a child at grade school becomes ill and is taken to the nearest medical facility, the system can contact the parent/guardian of the child based on the social media profile connection.

A detailed description of embodiments of the claimed structures and methods are disclosed herein; however, it is to be understood that the disclosed embodiments are merely illustrative of the claimed structures and methods that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether or not explicitly described.

Figure 1:
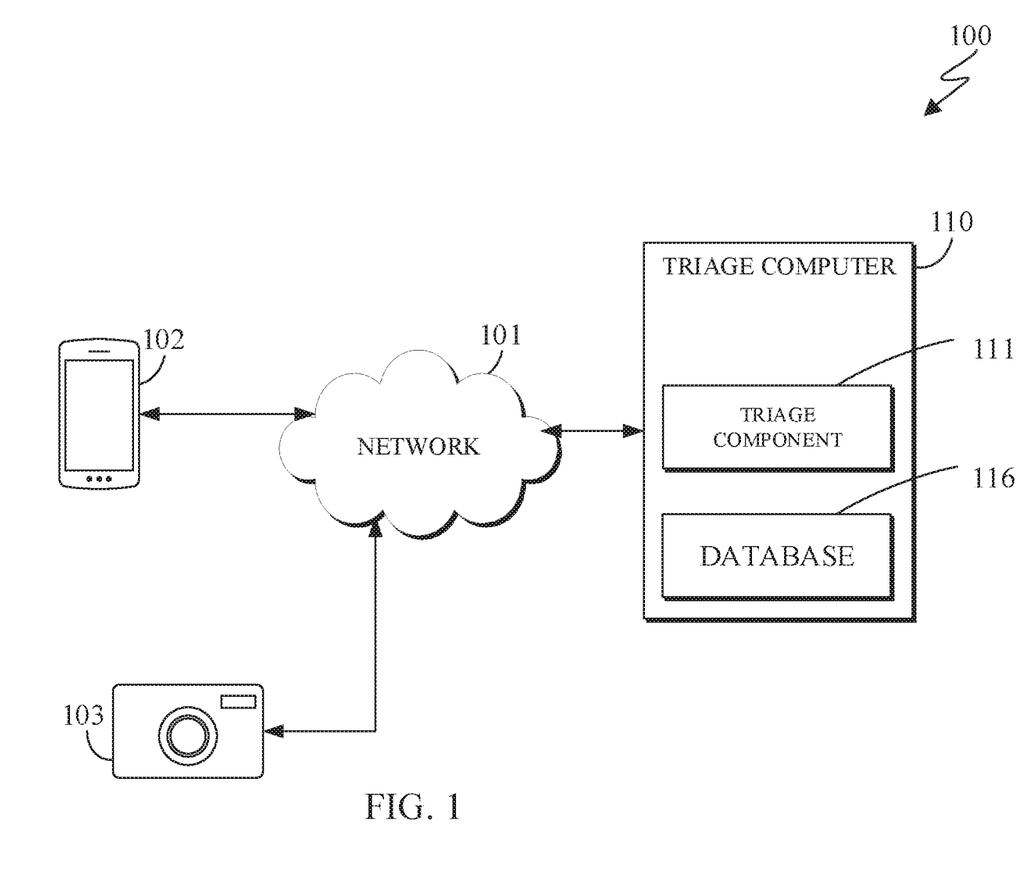
FIG. 1 is a functional block diagram illustrating a topology of a triage environment, designated as 100, in accordance with an embodiment of the present invention.

FIG. 1 is a functional block diagram illustrating a topology of a triage detection environment, designated as 100, in accordance with an embodiment of the present invention. FIG. 1 provides only an illustration of one implementation and does not imply any limitations with regard to the environments in which different embodiments may be implemented. Many modifications to the depicted environment may be made by those of ordinary skill in the art without departing from the scope of the invention as recited by the claims.

Triage detection environment 100 includes mobile device 102, IoT (Internet of Things) device 103, and triage computer 110. All (e.g., 102, 103 and 110) elements can be interconnected over network 101.

Network 101 can be, for example, a telecommunications network, a local area network (LAN), a wide area network (WAN), such as the Internet, or a combination of the three, and can include wired, wireless, or fiber optic connections. Network 101 can include one or more wired and/or wireless networks that are capable of receiving and transmitting data, voice, and/or video signals, including multimedia signals that include voice, data, and video information. In general, network 101 can be any combination of connections and protocols that can support communications between triage computer 110 and other computing devices (not shown) within triage detection environment 100. It is noted that other computing devices can include, but is not limited to, mobile device 102, IoT device 103 and any electromechanical devices capable of carrying out a series of computing instructions.

Mobile device 102 can represent a network capable mobile computing device that may receive and transmit confidential data over a wireless network. Mobile computing device 102 can be a laptop computer, tablet computer, netbook computer, personal computer (PC), a personal digital assistant (PDA), a smart phone, smart watch (with GPS location) or any programmable electronic device capable of communicating with other computers (e.g., triage computer 110) via network 101, in accordance with an embodiment of the present invention.

IoT device 103 is an IoT device such as, but is not limited to, a smart camera, a monitor and other smart sensors.

Triage computer 110 can be a standalone computing device, a management server, a web server, a mobile computing device, or any other electronic device or computing system capable of receiving, sending, and processing data. In other embodiments, triage computer 110 can represent a server computing system utilizing multiple computers as a server system, such as in a cloud computing environment. In another embodiment, triage computer 110 can be a laptop computer, a tablet computer, a netbook computer, a personal computer (PC), a desktop computer, a personal digital assistant (PDA), a smart phone, or any other programmable electronic device capable of communicating with other computing devices (not shown) within triage detection environment 100 via network 101. In another embodiment, triage computer 110 can represent a computing system utilizing clustered computers and components (e.g., database server computers, application server computers, etc.) that act as a single pool of seamless resources when accessed within triage detection environment 100.

Triage computer 110 can include triage component 111 and database 116.

Triage component 111 can enable embodiments of the present invention to capture data (e.g., images, videos and audio), recognize medical issues based on the captured data and search for an appropriate facility or responder. Triage component 111 will be described in greater details in regard to FIG. 2.

Database 116 can be a repository for data used by triage component 111. Database 116 can be implemented with any type of storage device capable of storing data and configuration files that can be accessed and utilized by triage computer 110, such as a database server, a hard disk drive, or a flash memory. Database 116 can use one or more of a plurality of techniques known in the art to store a plurality of information. In the depicted embodiment, database 116 resides on triage computer 110. In another embodiment, database 116 may reside elsewhere within triage detection environment 100, provided triage component 111 has access to database 116. Database 116 may store information associated with, but is not limited to, corpus knowledge of medical symptoms, medical facility location including treatment availability, and medical skills including history of the responders.

Figure 2:
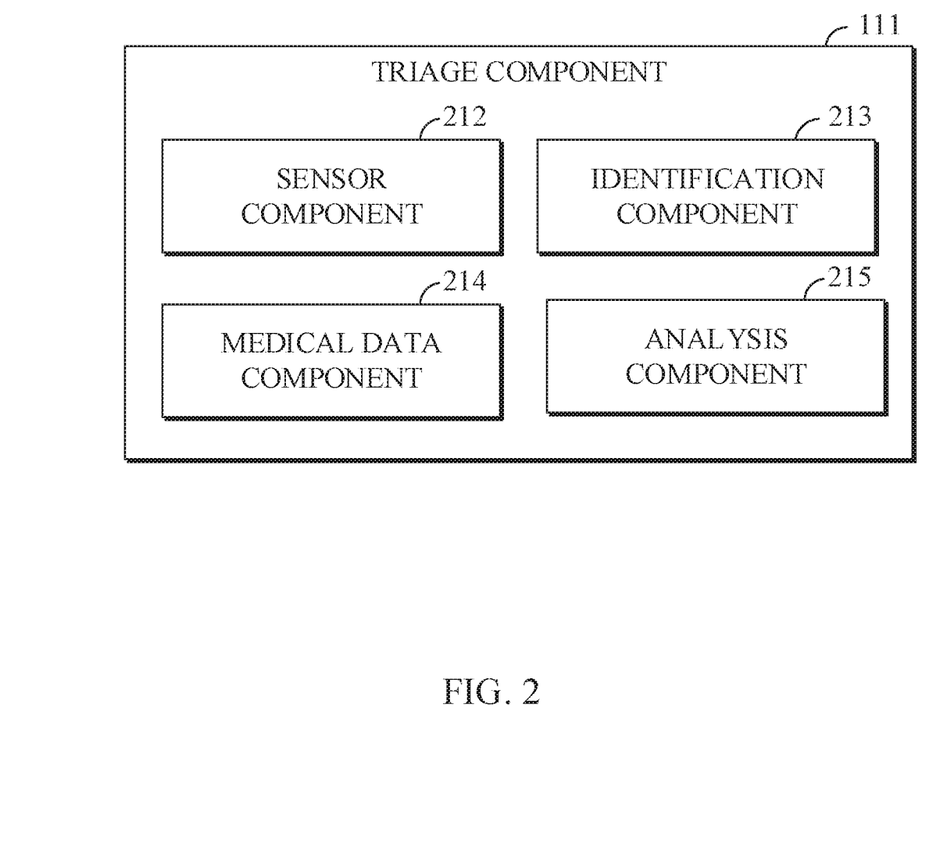
FIG. 2 is a functional block diagram illustrating a triage component, in accordance with an embodiment of the present invention.

FIG. 2 is a functional block diagram illustrating triage component 111 in accordance with an embodiment of the present invention. In the depicted embodiment, triage component 111 can include sensor component 212, identification component 213, medical data component 214 and analysis component 215. It is noted that triage component 111 can be utilized as an application (front end interface) on mobile computing devices. The application implemented on the mobile device may contain a user interface and functionality such as, but not limited to, "RECORD EVENT IN PROGRESS" (i.e., record the vehicle accident scene in real-time), "SEND EVENT LOCATION" (i.e., send the location coordinates to the emergency responders and/or the back end server of the system) and "REQUEST RESPONDER" (i.e., request emergency responder to the location of the user).

As is further described herein below, sensor component 212 can provide the capability of communicating to various sensors (e.g., cameras, microphones, location, etc.) embedded in mobile device 102 and IoT device 103 located in the triage detection environment 100. Additionally, sensor component 212 can access and retrieve data associated with the previously mentioned sensors. For example, a hypothetical car accident scenario will be used to illustrate the functionality of all subcomponents belonging to triage component 111. There has been a multiple car accident. Car A hits Car B on a single lane road. The accident further caused Car B to hit Car C which was in the lane next to Car B. Driver A of Car A did not suffer any injuries and accordingly, did not require medical assistance. However, Driver B and Driver C were not able to leave the crashed vehicle due to their injuries (e.g., head blunt force trauma from the deployed airbags, laceration from the broken windshield, etc.). There are several passersby who have stopped to offer assistance. Some of the passersby have called the emergency number (i.e., 911) to request emergency medical assistance and some passersby are recording images with their mobile devices (i.e., mobile device installed with an application of the present invention) of the scene and the injured individuals. As previously mentioned, sensor component 212 can communicate with various computing devices (e.g., mobile device 102 and IoT device 103) at the accident scene. Thus, sensor component 212 can retrieve images, videos and audio from mobile devices belonging to the passersby and any other devices belonging to the soon-to-be arrived emergency responders. Sensor component 212 can retrieve GPS (Global Positioning System) data associated with mobile device 102 and/or IoT device 103. Sensor component 212 can also retrieve GPS data from vehicles equipped with a location tracking system. For example, using the previously mentioned car accident scenario, an emergency responder vehicle arrives at the scene and is equipped with IoT devices and a GPS location tracker. Sensor component 212 can retrieve location data from the emergency vehicle's GPS and other data from the built-in IoT devices. It is noted that sensor component 212 does not have to rely on GPS, sensor component 212 can use indirect methods such as Wi-Fi, mobile phone towers, etc. to determine the location of the accident, location of healthcare facilities or location of medical personnel. Furthermore, sensor component 212 can store retrieved data in database 116.

As is further described herein below, identification component 213 can provide the capability of detecting and identifying objects from sensor component 212. Sensor component 212 can contain information associated with the various sensors (e.g., camera, microphones, location, etc.). Using existing techniques known in the art of medical image identification based on video/graphics analysis (e.g., deep learning by IBM® Watson Health, etc.), identification component 213 can identify injuries such as, but not limited to, lacerations, compound bone fractures and ligament sprains. For example, referring to the previously mentioned car accident scenario, identification component 213, through sensor component 212, begins to analyze images from the car accident related to the victims (e.g., Driver B and Driver C) and can identify the injuries. The images of Driver C (and pictures of Car C) show several lacerations on the face and arms of Driver C from the broken windshield. Identification component 213 can determine (based on the images and/or audio cues) that the laceration is not deep enough to require immediate medical attention. Images of Car B show a crushed front end and an unresponsive Driver B in the driver seat in front of a deflated airbag. Identification component 213 was able to analyze additional images of Car B and Driver B, and can identify deep tissue bruising around the head and thoracic area of Driver B. Identification component 213 can determine (based on the images and/or audio cues) that the deep tissue bruising is not serious enough to require immediate medical attention.

As is further described herein below, medical data component 214 provides a corpus of medical knowledge based on existing references of known medical injuries and associated treatments of those injuries. Medical data component 214 can accumulate the collected data from identification component 213 via sensor component 212 and based on the collected data, medical data component 214 can build a corpus of knowledge of new injuries and treatments. Furthermore, medical data component 214 can retrieve data from a database server (i.e., central repository of medical related information) and/or from database 116. Medical data component 214 can contain a registry of emergency responders/personnel (e.g., police, fireman, emergency medical professionals, etc.), other medical personnel (e.g., doctors, nurses, medical specialist, etc.) and health care institutions (e.g., hospitals, emergency medical facilities, clinics, etc.). The registry (e.g., emergency responders/personnel, other medical personnel, etc.) can contain the following information, but it is not limited to, name including contact information (e.g., phone number, email and address, etc.), medical specialty, years of experience in the medical treatment (either general or specific type of injury), primary location including attached hospitals/clinics, social media profile and status indicator (i.e., availability). It is noted that the medical personnel/respondent contained within the registry (e.g., list) has given consent to share information including their social media profile.

Additionally, medical data component 214 can contain information associated with a health care institution regarding blood type available at the healthcare institution, medical equipment available, number of emergency room and non-emergency room beds available, available nursing staff and medical supplies available.

As is further described herein below, analysis component 215 of embodiments of the present invention can provide, in real time, the capability of determining, qualified medical personnel closest (i.e., pre-determined distance that can be adjustable) to the accident scene and/or injured individual of the accident based on several factors. These factors include, but are not limited to, a) status of the injured individual, identified using images of the accident location and audio cues/clues from the injured individual and other people at the accident location; b) severity of the accident and time of the accident to determine the criticality of the injured individual and accessibility to the accident location; c) specialization of the corresponding medical personnel required based on b; d) history of trauma cases handled by the medical personnel identified in c matching the injured individual's condition; e) the injured individual's family doctor or an acquaintance of the family doctor, can be identified based on a social media profile or past treatments of the injured individual; f) other external factors such as, but not limited to, access to the accident location; and g) audio and video clues associated with the damage to the vehicle where the injured individual was positioned.

For example, using the previously mentioned car accident scenario to illustrate the functionality of analysis component 215, driver B shows deep tissue bruising around the head and thoracic region, Car B shows a crushed front end and an unresponsive Driver B in the driver seat in front of a deflated airbag and accordingly, Driver B is deemed to be the most critically injured by analysis component 215. Further, there are three healthcare facilities within a 10-mile radius of the car accident. The first facility is Hospital A, which has Doctor A, who specializes in treating blunt force trauma and has over 10 years of experience in the field. Additionally, Hospital A contains a trauma center ward on site. The second facility is Hospital B, which has Doctor B. Hospital B contains an advanced cardiac surgery ward. Additionally, Doctor B specializes in cardiac and thoracic surgery with over 15 years of surgical experience. The third facility, Clinic C, has Doctor C. Clinic C specializes in general healthcare and treatment. Doctor C has experience in internal medicine and would be considered a general practitioner. Additionally, Doctor C is the family doctor for Driver C and has been the primary care doctor for Driver C for 20 years. The system, through analysis component 215, decides (initial assessment) based on at least one of the previously mentioned factors that Doctor A would be best suited for Driver B. It is noted that a healthcare list, which can contain a healthcare location in order of importance, can be generated during the initial assessment or final assessment by analysis component 215. The healthcare list can include, but it is not limited to, name of a facility, name of a medical professional, location of the facility and medical professional and blood type availability. It is possible that after the system has identified Doctor A, Driver B's condition declines (in a span of an hour) to where the system (continuously monitoring the injured individual's condition, healthcare facility, weather conditions, traffic/road/hazard conditions and doctor's availability) determines that Doctor B (surgeon) may be better suited to treat Driver B.

Furthermore, analysis component 215, in real-time, can identify and route the victim to the appropriate health care facility (e.g., hospital, clinic, medical camp, etc.) based on several factors. These factors include the following, but it is not limited to, a) equipment and/or centers at the healthcare facility to treat the current state of the victim; b) appropriate doctor available at the healthcare facility to treat the current status of the victim; c) availability of blood type of the injured individual and if not available, the possibility of procuring the injured individual's blood type, d) external factors such as, but not limited to, climatic conditions to determine access to the accident location; and f) diagnosis of the person/doctor giving immediate first aid at the accident location. For example, using the previously mentioned car accident scenario to illustrate the functionality of analysis component 215, Driver C shows several lacerations around the face and arms and is deemed to be the least critically injured by analysis component 215. The system, through analysis component 215, decides, based on at least one of the previously mentioned factors, that Doctor C (located at Clinic C) would be best suited to treat Driver C. Clinic C specializes in general healthcare and treatment. Doctor C has experience in internal medicine and would be considered a general practitioner. Additionally, Doctor C is the family doctor for Driver C and has been the primary care doctor for Driver C for 20 years.

Figure 3:
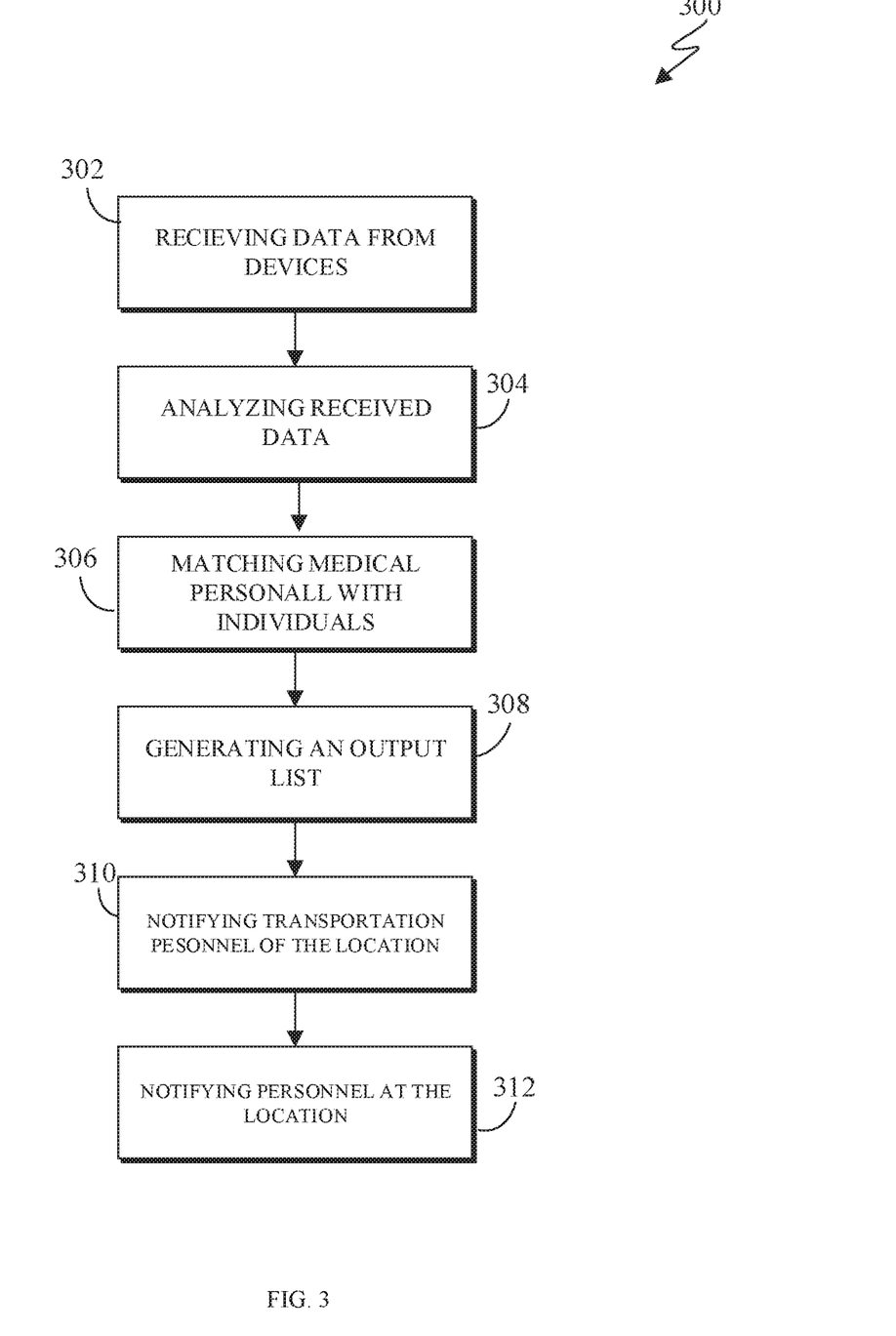
FIG. 3 is a flowchart illustrating the operation of a triage management system, designated as 300, in accordance with an embodiment of the present invention.

FIG. 3 is a flowchart illustrating the operation of a triage detection environment 100, designated as 300, in accordance with an embodiment of the present invention.

Triage component 111 receives data from devices (step 302) associated with an event. In an embodiment, triage component 111 through sensor component 212 retrieves image and audio related data from the devices (e.g., mobile device 102, IoT device 103) associated with the event. For example, referring to the multiple car accident scenario, passersby have recorded audio and images of the accident. Sensor component 212 can retrieve the audio, image and location data associated with the accident.

Triage component 111 analyzes the received data (step 304). In an embodiment, triage component 111 through object identification component 213 determines any objects of interest in the received video data. For example, referring to the multiple car accident, the triage component 111 can identify lacerations to the injured individual, broken windshields/crushed doors of the vehicle and blunt force trauma to the injured individual.

Triage component 111 matches one or more medical personnel with the injured individuals from the event (step 306). In an embodiment, triage component 111 through analysis component 215 analyzes the retrieved data and matches corresponding medical personnel suited to treat the injured individuals. For example, referring to the multiple car accident, the system can match Doctor A with Driver B and can match Doctor C with Driver C.

In another embodiment, triage component 111, through analysis component 215, can notify passing medical personnel of the event based on the medical personnel's proximity to the event location and skills of the medical personnel in relation to the injuries of the injured individual. For example, referring to the multiple car accident, analysis component 215 determines the injuries for Driver B and Driver C. Doctor D (has a profile on the medical database) is on his way to hospital D to start his rounds and will pass the accident scene. The analysis component 215 can determine that Doctor D will be passing by the accident scene in 15 minutes and Doctor D has the capability of treating Driver B, the triage component 111 notifies Doctor D of the accident and Doctor D can stop to render assistance.

Triage component 111 generates an output list (step 308). In an embodiment, triage component 111 generates a list (i.e., healthcare list) based on the prior matching, step 306. The output list can include, but it is not limited to, the location of a healthcare facility along with corresponding medical personnel, medical personnel in the vicinity of the event and medical transportation vehicles within the vicinity of the event. For example, referring to the multiple car accident, the system can generate a list which includes Doctor A, Doctor B, Doctor C, Hospital A, Hospital B and Hospital C.

Triage component 111 notifies transportation personnel of the healthcare facility location (step 310). In an embodiment, triage component 111, based on the generated list, notifies the transportation personnel of the location of the healthcare facility to transport the injured individual. For example, referring to the multiple car accident, the triage component 111 can notify transport personnel (i.e., Ambulance B) to take Driver B (i.e., injured individual) to Hospital A. Furthermore, triage component 111 can concurrently route Ambulance C to take Driver C to Doctor C/Hospital C and route any other medical transport vehicle to their respective medical facility.

In another embodiment, triage component 111 can instruct autonomous vehicles to transport injured individuals to a healthcare facility instead of notifying transportation personnel of the location. For example, an autonomous vehicle, Ambulance D, with a medical emergency personnel, EMS 1, on board arrives at the car accident scene. EMS 1 places/loads Driver C into Ambulance D. Triage component 111 instructs Ambulance D to transport Driver C to Hospital C while EMS 1 is helping/triaging other injured individuals.

Triage component 111 notifies the medical personnel at the location (step 312). In an embodiment, triage component 111, notifies the medical personnel at the receiving location (i.e., the healthcare facility) that there is an incoming transport of an injured individual. For example, referring to the multiple car accident, the system can notify medical personnel (including Doctor A) at Hospital A of the incoming injured individual, Driver B.

The present invention may be a system, a method, and/or a computer program product. The computer program product may include a computer readable storage medium (or media) having computer readable program instructions thereon for causing a processor to carry out aspects of the present invention.

Figure 4:
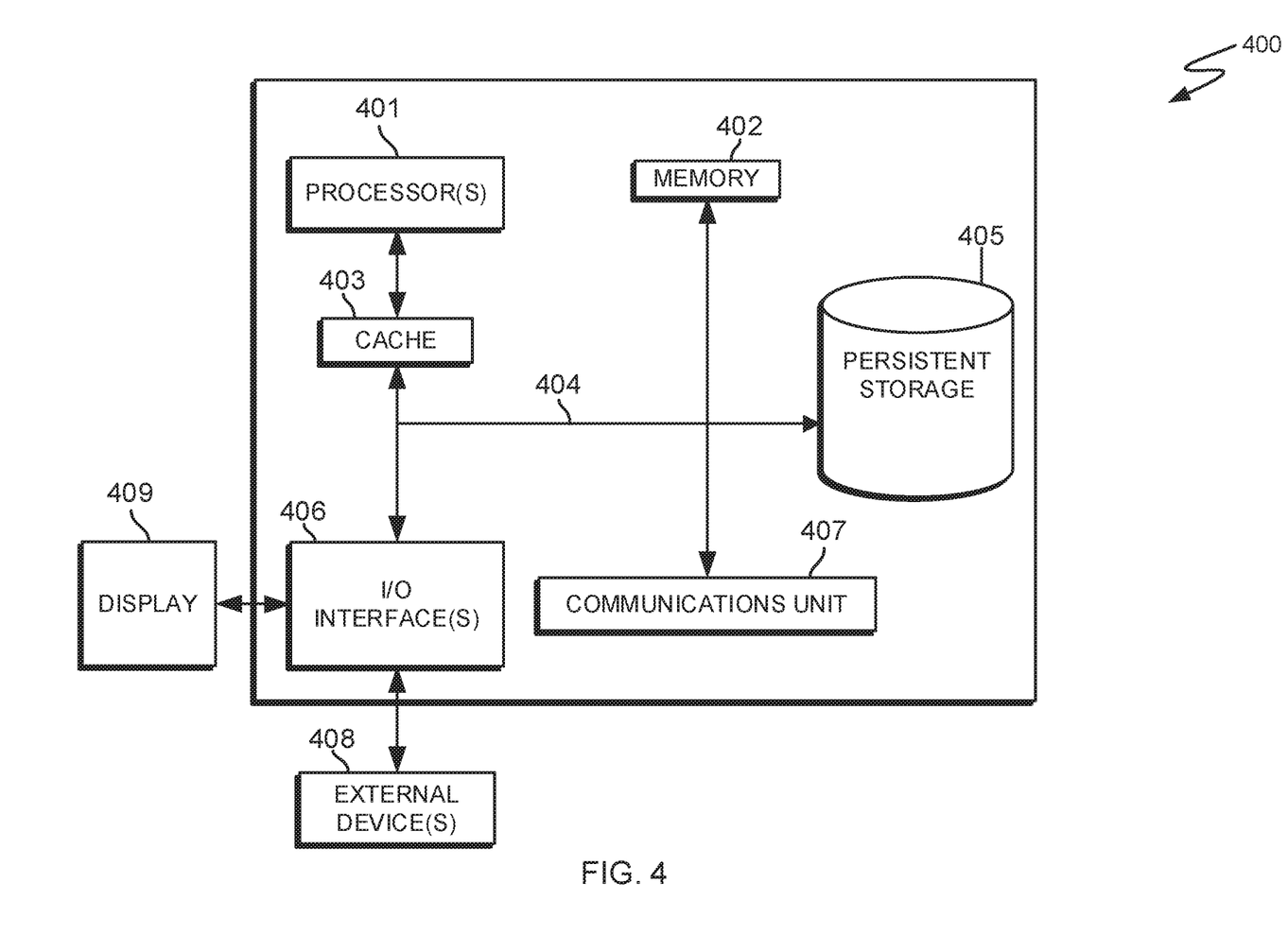
FIG. 4 depicts a block diagram, designated as 400, of components of a computer capable of executing the triage management system within the triage environment of FIG. 1, in accordance with an embodiment of the present invention.

FIG. 4 depicts a block diagram of components of Triage component 111 application, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

FIG. 4 includes processor(s) 401, cache 403, memory 402, persistent storage 405, communications unit 407, input/output (I/O) interface(s) 406, and communications fabric 404. Communications fabric 404 provides communications between cache 403, memory 402, persistent storage 405, communications unit 407, and input/output (I/O) interface(s) 406. Communications fabric 404 can be implemented with any architecture designed for passing data and/or control information between processors (such as microprocessors, communications and network processors, etc.), system memory, peripheral devices, and any other hardware components within a system. For example, communications fabric 404 can be implemented with one or more buses or a crossbar switch.

Memory 402 and persistent storage 405 are computer readable storage media. In this embodiment, memory 402 includes random access memory (RAM). In general, memory 402 can include any suitable volatile or non-volatile computer readable storage media. Cache 403 is a fast memory that enhances the performance of processor(s) 401 by holding recently accessed data, and data near recently accessed data, from memory 402.

Program instructions and data (e.g., software and data ×10) used to practice embodiments of the present invention may be stored in persistent storage 405 and in memory 402 for execution by one or more of the respective processor(s) 401 via cache 403. In an embodiment, persistent storage 405 includes a magnetic hard disk drive. Alternatively, or in addition to a magnetic hard disk drive, persistent storage 405 can include a solid state hard drive, a semiconductor storage device, a read-only memory (ROM), an erasable programmable read-only memory (EPROM), a flash memory, or any other computer readable storage media that is capable of storing program instructions or digital information.

The media used by persistent storage 405 may also be removable. For example, a removable hard drive may be used for persistent storage 405. Other examples include optical and magnetic disks, thumb drives, and smart cards that are inserted into a drive for transfer onto another computer readable storage medium that is also part of persistent storage 405. Triage component 111 can be stored in persistent storage 405 for access and/or execution by one or more of the respective processor(s) 401 via cache 403.

Communications unit 407, in these examples, provides for communications with other data processing systems or devices. In these examples, communications unit 407 includes one or more network interface cards. Communications unit 407 may provide communications through the use of either or both physical and wireless communications links. Program instructions and data (e.g., triage component 111) used to practice embodiments of the present invention may be downloaded to persistent storage 405 through communications unit 407.

I/O interface(s) 406 allows for input and output of data with other devices that may be connected to each computer system. For example, I/O interface(s) 406 may provide a connection to external device(s) 408, such as a keyboard, a keypad, a touch screen, and/or some other suitable input device. External device(s) 408 can also include portable computer readable storage media, such as, for example, thumb drives, portable optical or magnetic disks, and memory cards. Program instructions and data (e.g., triage component 111) used to practice embodiments of the present invention can be stored on such portable computer readable storage media and can be loaded onto persistent storage 405 via I/O interface(s) 406. I/O interface(s) 406 also connect to display 409.

Display 409 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method for triaging injured individuals, the computer-implemented method comprising:

receiving, by one or more computer processors, data from one or more mobile computing devices associated with one or more injured individuals at an event, wherein data comprises a first location, video data and audio data;

analyzing, by the one or more computer processors, the received data;

matching, by the one or more computer processors, one or more medical personnel with the one or more injured individuals of the event, further comprising:

retrieving, by the one or more computer processors, a medical personnel list from a database wherein the medical personnel list further comprises name, medical skills, history, location and availability;

retrieving, by the one or more computer processors, a healthcare location list from a database wherein the health care list further comprises name, location and blood type availability; and matching, by the one or more computer processors, the one or more injured individuals, via machine learning, to the one or medical personnel based on the first location, the severity of injuries, location of the one or more medical personnel, a healthcare location, blood type of the injured individuals, the blood type availability at the healthcare location and the medical skills associated with the one or more medical personnel;

generating, by the one or more computer processors, an output list, wherein the output list comprises a second location to transport at least one of the one or more injured individuals;

notifying, by the one or more computer processors, one or more transportation personnel of the second location for transporting the at least one of the one or more injured individuals; and notifying, by the one or more computer processors, one or more healthcare facility personnel at the second location of the arrival of the at least one of the one or more injured individuals.

2. The computer-implemented method of claim 1 further comprising:

instructing, by the one or more computer processors, an autonomous vehicle to transport the one or more injured individuals based on the output list.

3. The computer-implemented method of claim 1, wherein receiving data from the one or more mobile computing devices, further comprises:

receiving, by the one or more computer processors, a first video, a first image and a first audio recording based on the mobile device associated with the one or more injured individuals; and receiving, by the one or more computer processors, a second video, a second image and a second audio recording based on the mobile device associated with one or more individuals at the event, wherein the one or more individuals comprises medical emergency responders, police personnel and passersby.

4. The computer-implemented method of claim 1, wherein the event further comprises multiple vehicle accidents, train accidents, boat accidents and airplane accidents.

5. The computer-implemented method of claim 1, wherein analyzing data further comprises:

determining, by the one or more computer processors, damage to one or more vehicles associated with the one or more injured individuals based on the received video and audio data;

determining, by the one or more computer processors, severity of injuries associated with the one or more injured individuals based on the received video data, audio data and the damage to the one or more vehicles; and determining, by the one or more computer processors, the first location, wherein the first location comprises an injured individual location and a vehicle location associated with the event.

6. The computer-implemented method of claim 1, further comprising:

notifying, by the one or more computer processors, a medical professional passing by the event associated with the one or more injured individuals.

7. The computer-implemented method of claim 1, further comprising:

generating, by the one or more computer processors, a third location based on the matched of the one or more medical personnel with the at least one of the one or more injured individuals, wherein the third location is based on a proximity between a healthcare location and the first location of the one or more medical personnel, the first location of injured individual, weather condition, traffic and road condition.

8. A computer program product for triaging injured individuals, the computer program product comprising:

one or more computer readable storage media and program instructions stored on the one or more computer readable storage media, the program instructions comprising:

program instructions to receive data from one or more mobile computing devices associated with one or more injured individuals at an event, wherein data comprises a first location, video data and audio data;

program instructions to analyze the received data;

program instructions to match one or more medical personnel with the one or more injured individuals of the event, further comprising:

program instructions to retrieve a medical personnel list from a database wherein the medical personnel list further comprises name, medical skills, history, location and availability;

program instructions to retrieve a healthcare location list from a database wherein the health care list further comprises name, location and blood type availability; and program instructions to match the one or more injured individuals, via machine learning, to the one or medical personnel based on the first location, the severity of injuries, location of the one or medical personnel, a healthcare location, blood type of the injured individuals, the blood type availability at the healthcare location and the medical skills associated with the one or more medical personnel;

program instructions to generate an output list, wherein the output list comprises a second location to transport at least one of the one or more injured individuals;

program instructions to notify one or more transportation personnel of the second location for transporting the at least one of the one or more injured individuals; and program instructions to notify one or more healthcare facility personnel at the second location of the arrival of the at least one of the one or more injured individuals.

9. The computer program product of claim 8, further comprising:

program instructions to instruct an autonomous vehicle to transport the one or more injured individual based on the output list.

10. The computer program product of claim 8, wherein program instructions to receive data from the one or more mobile computing devices further comprises:

program instructions to receive a first video, a first image and a first audio recording based on the mobile device associated with the one or more injured individuals; and program instructions to receive a second video, a second image and a second audio recording based on the mobile device associated with one or more individuals at the event, wherein the one or more individuals comprises medical emergency responders, police personnel and passersby.

11. The computer program product of claim 8, wherein the event further comprises of multiple vehicle accidents, train accidents, boat accidents and airplane accidents.

12. The computer program product of claim 8, wherein program instructions to analyze data further comprises:

program instructions to determine a damage to one or more vehicle associated with the one or more injured individuals based on the received video and audio data;

program instructions to determine severity of injuries associated with the one or more injured individuals based on the received video data, audio data and the damage to the one or more vehicle; and program instructions to determine the first location, wherein the first location comprises an individual location and a vehicle location associated with the event.

13. The computer program product of claim 8,
program instructions to notify, a medical professional passing by the event associated with the one or more injured individuals.

14. The computer program product of claim 8, further comprising:
program instructions to generate a third location based on the matched of the one or more medical personnel with the one or more injured individual, wherein the third location is based on proximity between a healthcare location and a location of the one or more medical personnel, the first location of the one or more injured individuals, weather condition, traffic and road condition.

15. A computer system for triaging injured individuals, the computer system comprising:
one or more computer processors;
one or more computer readable storage media; and
program instructions stored on the one or more computer readable storage media for execution by at least one of the one or more computer processors, the program instructions comprising:
program instructions to receive data from one or more mobile computing devices associated with one or more injured individuals at an event, wherein data comprises a first location, video data and audio data;
program instructions to analyze the received data;
program instructions to match one or more medical personnel with the one or more injured individuals of the event, further comprising:
program instructions to retrieve a medical personnel list from a database wherein the medical personnel list further comprises name, medical skills, history, location and availability;
program instructions to retrieve a healthcare location list from a database wherein the health care list further comprises name, location and blood type availability; and
program instructions to match the one or more injured individuals, via machine learning, to the one or medical personnel based on the first location, the severity of injuries, location of the one or medical personnel, a healthcare location, blood type of the injured individuals, the blood type availability at the healthcare location and the medical skills associated with the one or more medical personnel;
program instructions to generate an output list, wherein the output list comprises a second location to transport at least one of the one or more injured individuals;
program instructions to notify one or more transportation personnel of the second location for transporting the at least one of the one or more injured individuals; and
program instructions to notify one or more healthcare facility personnel at the second location of the arrival of the at least one of the one or more injured individuals.

16. The computer system of claim 15, further comprising:
program instructions to instruct an autonomous vehicle to transport the one or more injured individuals based on the output list.

17. The computer system of claim 15, wherein program instructions to receive data from the one or more mobile computing devices further comprises:
program instructions to receive a first video, a first image and a first audio recording based on the mobile device associated with the one or more injured individuals; and
program instructions to receive a second video, a second image and a second audio recording based on the mobile device associated with one or more individuals at the event, wherein the one or more individuals comprises of medical emergency responders, police personnel and passersby.

18. The computer system of claim 15, wherein program instruction to analyze data further comprises:
program instructions to determine a damage to one or more vehicle associated with the one or more injured individuals based on the received video and audio data;
program instructions to determine severity of injuries associated with the one or more injured individuals based on the received video data, audio data and the damage to the one or more vehicle; and
program instructions to determine the first location, wherein the first location comprises an individual location and a vehicle location associated with the event.

19. The computer system of claim 18,
program instructions to notify, a medical professional passing by the event associated with the one or more injured individuals.

20. The computer system of claim 19, wherein generating an output list further comprising:
program instructions to generate the third location based on the matched of the one or more medical personnel with the one or more injured individual, wherein the third location is based on proximity between a healthcare location and the first location of the one medical personnel, the first location of the one or more injured individual, weather condition, traffic and road condition.

* * * * *